United States Patent
Maxim et al.

(10) Patent No.: US 7,191,901 B2
(45) Date of Patent: Mar. 20, 2007

(54) SUBSTRATE CONTAINER THAT DOES NOT DEGRADE SUBSTRATE SURFACE

(75) Inventors: Paul W. Maxim, Horseheads, NY (US); Kevin T. Morris, Hammondsport, NY (US); James B. Stamatoff, Painted Post, NY (US); Paul M. Szlosek, Kennebunk, ME (US)

(73) Assignee: Corning Incorporated, Corning, NY (US)

( * ) Notice: Subject to any disclaimer, the term of this patent is extended or adjusted under 35 U.S.C. 154(b) by 237 days.

(21) Appl. No.: 10/400,205

(22) Filed: Mar. 27, 2003

(65) Prior Publication Data

US 2004/0031712 A1    Feb. 19, 2004

Related U.S. Application Data

(60) Provisional application No. 60/403,789, filed on Aug. 15, 2002.

(51) Int. Cl.
B65D 85/48    (2006.01)

(52) U.S. Cl. .................... 206/456; 206/205; 206/524.1

(58) Field of Classification Search ................ 206/456, 206/524.3, 204, 205, 524.1; 424/102; 435/307.1; 211/41.14
See application file for complete search history.

(56) References Cited

U.S. PATENT DOCUMENTS

| | | | | |
|---|---|---|---|---|
| 3,532,604 A | * | 10/1970 | Bloch et al. ............. | 435/305.4 |
| 3,621,994 A | * | 11/1971 | Brown ........................ | 206/446 |
| 4,589,511 A | | 5/1986 | Hellon ........................ | 206/456 |
| 4,635,791 A | * | 1/1987 | Jackson et al. ............. | 206/210 |
| 5,080,225 A | * | 1/1992 | Russo et al. ................ | 206/204 |
| 5,090,568 A | * | 2/1992 | Tse ............................. | 206/456 |
| 5,098,618 A | * | 3/1992 | Zelez ......................... | 264/446 |
| 6,171,780 B1 | * | 1/2001 | Pham et al. .................. | 435/4 |
| 6,348,965 B1 | * | 2/2002 | Palladino et al. ......... | 356/243.1 |
| 6,361,745 B1 | * | 3/2002 | Regan et al. ............... | 422/104 |
| 2001/0053418 A1 | * | 12/2001 | Saga ........................ | 427/412.3 |
| 2002/0008045 A1 | * | 1/2002 | Guyot et al. ................ | 206/456 |
| 2003/0198968 A1 | * | 10/2003 | Matson .......................... | 435/6 |
| 2004/0086874 A1 | * | 5/2004 | Parker ........................... | 435/6 |
| 2004/0096914 A1 | * | 5/2004 | Fang et al. .................. | 435/7.9 |
| 2004/0142365 A1 | * | 7/2004 | Bao et al. ...................... | 435/6 |

FOREIGN PATENT DOCUMENTS

EP    0 726 212    8/1996

* cited by examiner

Primary Examiner—Eugene Kim
Assistant Examiner—Urszula M. Cegielnik
(74) Attorney, Agent, or Firm—Thomas R. Beall; Melissa K. Dobson

(57) ABSTRACT

Packages and methods for containing slides adapted for the attachment of biomolecules. The containers do not degrade the ability of biomolecules to attach to the surface when the slides are stored or shipped in the container.

2 Claims, 8 Drawing Sheets

SUBSTRATE CONTAINER THAT DOES NOT DEGRADE SUBSTRATE SURFACE

This application claims the benefit of U.S. Provisional Application No. 60/403,789 filed Aug. 15, 2002, the entirety of which is incorporated herein by reference.

FIELD OF THE INVENTION

This invention relates to containers for packaging a plurality of substrates used in biological experiments. More particularly, the present invention relates to a substrate container that does not degrade the surface of the substrates.

BACKGROUND OF THE INVENTION

A wide variety of bioassays involve the binding or attachment of biomolecules, such as nucleic acids or proteins, on substrates. For example, microarrays are arrays of very small sample biomolecules, such as DNA or protein target material attached or bound as small spots on a solid substrate, typically a glass slide similar to a microscope slide. The attached or bound spots in the array are exposed to complementary genetic or protein probe samples derived from entities that have been tagged with fluorescent dyes. The probe material binds selectively to target spots where complementary bonding sites occur from a process called hybridization. Dissimilar probe molecules will not bind to the target molecules and will be washed away in a subsequent rinsing process. By measuring the quantity of bound probe molecules, a researcher can determine the affinity between the probe and the target molecules. This technique is used to measure a variety of biological characteristics including gene expression, genotype and gene sequence.

After hybridization, microarrays are imaged or scanned in an apparatus that illuminates the probe biomolecules with light which excites the fluors in the probe DNA causing the fluors to fluoresce. The brightness of each specimen or spot in the microarray is a function of the fluor density in that specimen or spot. The fluor density is, in turn, a function of the binding affinity of the probe molecule to the target molecule for each spot.

The surface chemistry and the surface morphology of the microarray substrate is a factor that impacts the quality of microassay readings. The surfaces of both organic and inorganic substrates are typically modified by the deposition of a coating or a polymeric monolayer film to improve binding or attachment of biomolecules, promote adhesion and lubrication, modify the electrical and optical properties of the substrate surface, and create electroactive films suitable for various optical and electronic sensors and devices. Poor quality substrates result in low DNA binding efficiency, poor spot morphology, and fluorescent background that can be unacceptably high and nonuniform. Microarray substrates are susceptible to damage and degradation of the surface chemistry if they are not stored properly. Therefore, there is a need for a way to store microarray substrates so that they are not degraded or damaged over time.

SUMMARY

The present invention generally provides packages and methods that utilize containers that do not degrade the ability of biomolecules to bind or attach to the surface of substrates such as slides. According to certain embodiments, the packages or containers and methods do not degrade the ability to detect the attachment of biomolecules to the substrates stored and/or shipped within the containers. It is to be understood that both the foregoing general description and the following detailed description are exemplary and are intended to provide further explanation of the invention as claimed.

DETAILED DESCRIPTION

Before describing several exemplary embodiments of the invention, it is to be understood that the invention is not limited to the details of construction or process steps set forth in the following description. The invention is capable of other embodiments and of being practiced or carried out in various ways.

Figure 1:
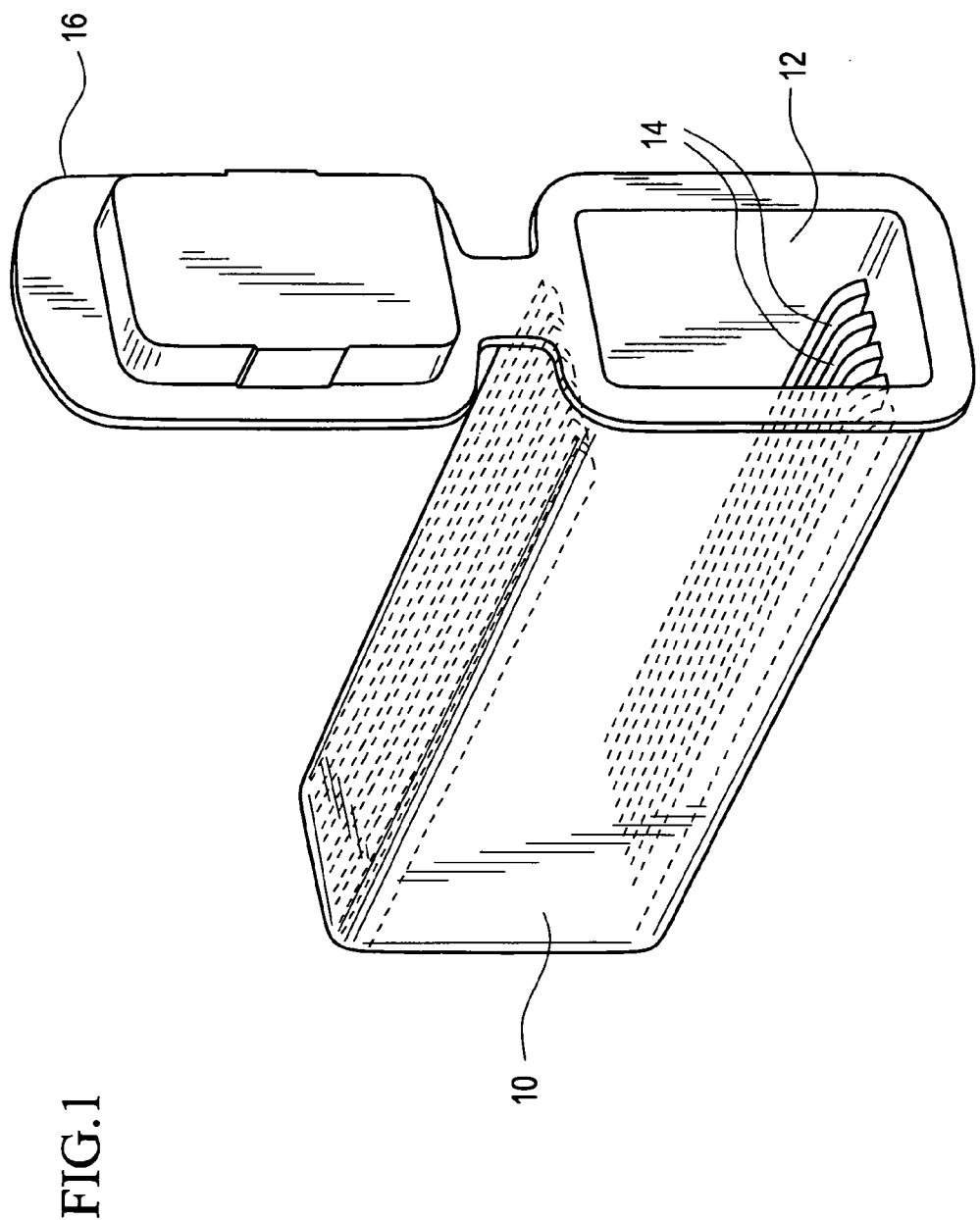
FIG. 1 is a perspective view of a container for storing and/or shipping substrates used for attaching or binding molecules thereto.

FIG. 1 shows an example of a container 10 for shipping and/or storing substrates used for immobilizing biomolecules. The container 10 defines an enclosure 12 for storing a plurality of substrates, which are typically glass slides (not shown), therein. To prevent damage to the surfaces, which typically include a coating or monolayer for promoting biomolecular adhesion, the enclosure 12 includes a plurality of slots 14 or other suitable means for storing slides in a spaced relationship. The container 10 may further include a lid 16 or other means for closing the container 10 to keep the slides in an environment free from dirt and dust during shipping and storage. The package should also be designed in a manner that prevents generation of dust during loading of the substrate in the container. In the embodiment shown, the container 10 includes five slots 14 for storing slides within the enclosure 12. However, the present invention is not limited to a container with any particular number of slots. In addition, while the container shown in FIG. 1 is rectangular, the invention is not limited to any particular container shape.

The various embodiments of the present invention are useful for storing and shipping a wide variety of substrates used for attaching or binding biological material thereto. One particular example of an application for which the containers of the present invention can be used is for the shipping and storage of microarray substrates, including, but not limited to, substrates having a coating or monolayer to promote attachment of biomolecules and substrates having an array of biomolecules deposited on a surface of the substrates. Microarrays are typically printed on substrates in the form of glass slides including a monolayer or coating on a surface of the slides to promote binding or attachment of biomolecules. Other suitable substrate materials include, but are not limited to, quartz, silica, metals, semiconductor materials, polymeric and ceramic materials. Biomolecules include, but are not limited to, ribonucleic acids (RNA), deoxyribonucleic acids (DNA), synthetic oligonucleotides, antibodies, proteins, peptides, lectins, modified polysaccharides, synthetic composite macromolecules, functionalized nanostructures, synthetic polymers, modified/blocked nucleotides/nucleosides, modified/blocked amino acids, fluorophores, chromophores, ligands, chelates, and haptens.

The coatings or monolayers on the surface of the substrates or slides promote attachment and binding of biomolecules to the surfaces of the slides. Suitable coatings and monolayers and methods for applying these coatings and monolayers are known in the art. Examples of suitable coatings and monolayers include, but are not limited to, compounds with an amine functionality, such as silane compounds. A particular example of a coating or monolayer used for biological assay preparation is gamma amino propyl silane (GAPS), which may be deposited by a variety of known methods, including spin coating, spray coating, and dip coating. Other suitable coatings include, but are not limited to silsesquioxanes such as aminoalkyl silsesquioxanes, and polylysines.

It is desirable to have substantially identically sized spots containing a known quantity of a pre-determined set of captured biomolecules located on the substrate in a regular geometric array with low background fluorescence. Variability in spot size and high background levels can be problematic in biomolecule hybridization. Variability in spot size and high background levels can arise from non-uniformities in a slide's coating which, in turn, can result in a working surface whose hydrophilic/hydrophobic properties are non-uniform. In addition to variability across the surface of individual slides, variability of surface characteristics among differing manufacturing lots of slides is undesirable and factors contributing to such variability should be minimized.

Applicants have surprisingly discovered that the packaging containers used for shipping and storing substrates can contribute to the degradation of the slide surface having a coating or monolayer. Degradation of the surface in turn degrades the ability of biomolecules to attach to the surface of the slide. Degrading the ability of biomolecules to attach to the surface of the slide means that the biomolecules in solution will be deposited with varying spot sizes on the slide surface and will also result in variability among different manufacturing lots which are stored or shipped in containers that contribute to surface degradation.

Degradation of the surface may also include an unacceptably large increase in the background fluorescence of a slide when measured in a fluorescence scanner. High background signals interfere with the measurement of binding activity. Many of the containers for storing and shipping substrates presently used in the immobilization of biomolecules are made from commonly available commodity resins. These resins include, but are not limited to certain polypropylene, polystyrene and acrylo-nitrile-butadienestyrene (ABS). Applicants have performed extensive testing of GAPS coated slides stored with a variety of conventional slide packaging materials, and experiments have shown that several of these materials contribute to the degradation of contact angle and increase in background fluorescence of slides when measured in a microarray fluorescence scanner. Applicants have also discovered several materials, some of which include ABS materials and polystyrenes, that do not contribute to the surface degradation of the slides. While the present invention should not be limited by any particular theory, it is believed that outgassing of low molecular weight materials from the packages made from [certain] these materials are deposited on the slide surfaces, which changes the hydrophobicity of the surface and/or increases the background fluorescence of the slides. In order to obtain uniform spotting or deposition in the manufacture of microarrays, the water contact angle should be consistent across the surface of individual slides and among various manufacturing lots and background fluorescence should be as low as possible.

One embodiment of the invention relates to a biological slide package comprising a container that provides an enclosure for a plurality of slides which have a surface with a chemical coating or monolayer adapted to attach a biomolecule thereto. The container is adapted to hold the plurality of slides during shipping and storage of the package. The container is made from a material that does not degrade the ability of biomolecules to attach to the slide surface during shipping or storage of the slides for at least four weeks, and in certain embodiments, longer periods of time, such as, for example up to 6 months or longer. In addition, according to other embodiments, the container material does not alter the ability to read the attachment of biomolecules using fluorescence methods by significantly increasing the background fluorescence on the surface of the slides during storage or shipping of the substrates in the container. Suitable materials for the manufacture of the container include polymeric materials such as cyclic olefinic copolymers, polycarbonates, certain styrene compounds that do not contribute to slide surface degradation, polymethacrylates and certain acrylonitrile butadiene styrene (ABS) compounds that do not contribute to slide surface degradation.

According to another embodiment of the invention, a package for storing slides is provided which includes a container surrounding a plurality of slides which have a surface with a chemical coating or monolayer adapted to attach a biomolecule thereto. In some embodiments, the slides exhibit an increase in background fluorescence of less than about 300 RFU or 400% compared to slides coated and measured on the same day after being stored in the container for at least four weeks as measured in a fluorescence microarray scanner at a photomultiplier tube setting of about 750 volts and at a wavelength between about 525 nm and 535 nm. In other embodiments, the slides exhibit changes in background fluorescence after storage in the container for at least four weeks of less than about 250 RFU or 333%, 200 RFU or 267%, 150 RFU or 200%, 125 RFU or 167%, 100 RFU or 133% and 50 RFU or 66% compared to slides coated and measured on the same day as measured in a fluorescence microarray scanner at a photomultiplier tube setting of about 750 volts and at a wavelength between about 525 nm and 535 nm.

In other embodiments, the slides exhibit changes in background fluorescence of the slides after storage in the container for at least three months of less than about 300 RFU or 400%, 250 RFU or 333%, 200 RFU or 267%, 150 RFU or 200%, 125 RFU or 167%, 100 RFU or 133% and 75 RFU or 100% compared to slides coated and measured on the same day as measured in a fluorescence microarray scanner at a photomultiplier tube setting of about 750 volts and at a wavelength between about 525 nm and 535 nm. In still other embodiments, the slides exhibit a change in background fluorescence after storage in the container for about 2 weeks of less than about 300 RFU or 400%, 200 RFU or 267%, 150 RFU or 200%, 125 RFU or 167%, 100 RFU or 133%, 50 RFU or 66% and 25 RFU or 33% compared to slides coated and measured on the same day as measured by a fluorescence microarray scanner at a photomultiplier tube setting of about 750 volts and at a wavelength between about 525 nm and 535 nm.

Experiments monitoring the background fluorescence change of the samples revealed significant variation among different scanners, including scanners made by the same manufacturer and of the same model. Such variation made it difficult to formulate an absolute and reliable measure of an acceptable increase in fluorescence for the packaging materials. However, as described further in the Examples, applicants developed a testing protocol that quantifies the effect of different packaging configurations on background fluorescence that is independent of the scanner used in the test.

Other embodiments of the invention relate to methods of packaging slides which have a coating or monolayer on a surface thereof and adapted for the attachment of biomolecules to the surface comprising placing a plurality of the slides in a container that does not degrade the ability of biomolecules to attach or bind to the surfaces of the slides when the slides are stored in the container for at least four weeks. According to some embodiments, the slides do not exhibit an unacceptably large change in water contact angle or increase in background fluorescence after storage in the containers for up to 6 months.

According to certain embodiments, applicants have discovered that by selecting materials having low outgassing characteristics, shipping and storing packages and containers can be manufactured that will provide for extended shelf life of the slides having a coating or monolayer thereon without unacceptable change in the aqueous contact angle or increase in background fluorescence. A shelf life of several months, for example, at least 2 months, 3 to 6 months, and as long as 1 year or more is desirable with minimal degradation in water contact angle and increase in background fluorescence. Polymeric or plastic materials are preferred for the manufacture of containers because they are inexpensive and easy to produce by techniques such as blow molding and injection molding. Polymeric materials are also softer than glass substrates and do not chip the corners of the substrates causing particulate matter to collect on the slide surface. Although containers made from inorganic materials such as metal, glass and ceramics will not contribute to the degradation of slides stored therein, such materials are not practical alternatives because they are too expensive to use in the manufacture of shipping containers. One characteristic of one group of presently preferred polymeric materials for manufacturing packages according to certain embodiments of the invention include materials that have a low molecular weight distribution. Examples of materials that can be used in accordance with certain embodiments of the invention, include, but are not limited to, cyclic olefin copolymer materials such as the TOPAS® made by Ticona of Summit, N.J., acrylic materials such as polymethylmethacyrlates (e.g., Plexiglass® V825 available from ATOFINA Chemicals), styrene such as DOW STYRON 695 and Hunstman Styrene 101–300, and clear ABS such as Polylac PA-717C from Chi Mei Industries Co. Ltd.

Without intending to limit the invention in any manner, the present invention will be more fully described by the following examples.

EXAMPLES

Corning GAPS™ glass slides were obtained and slides were placed in close proximity to 1"×3"×1 mm injection molded slides of various polymeric resins shown in the table and figures in a sealed glass container. All glassware was thoroughly cleaned with oxygen plasma prior to testing and the containers were sealed with Parafilm® made by American National Can in Menasha, Wis., and stored at either room temperature or 50° C. The materials tested included a variety of polymeric materials and controls, which were sealed glass staining dishes.

The glass slides were removed and measured for change in water contact angle using deionized water using a standard laboratory goniometer. Slides were also measured for a change in background fluorescence using an Axon Instruments GenePix™ 4000A Microarray Scanner with a photomultiplier tube setting of 750 volts and at wavelengths of about 532 nm and 635 nm. Measurements were made on the glass slides the day they were coated with the GAPS™ coating and prior to being placed in proximity to the plastic slides, and these measurements are represented as "0" or "Day of Coat" in the Figures. Gold stain tests were also performed on the slides by placing slides in Colloidal Gold Total Protein stain (Blotting Grade manufactured by Bio-Rad Laboratories in Hercules, Calif.) overnight and then rinsing with water and drying with nitrogen. The stain attaches to an amine surface. Acceptable slides were those that exhibited an evenly stained surface. The results for all tests are summarized in Table I below.

TABLE I

| | | Control-Glass | AF Acrylic | H Styrene | D Styrene | Topas 1 | Topas 2 | PETG | A Polypro | F Polypro | LCP | Polycarbonate | Clear ABS | SBC |
|---|---|---|---|---|---|---|---|---|---|---|---|---|---|---|
| RT CA | | | | | | | | | | | | | | |
| 37–45 | 2 w | A | M | A | A | A | A | A | A | U | M | A | A | U |
| 40–48 | 4 w | A | M | A | A | A | A | A | A | U | M | A | A | U |
| 45–53 | 3 m | A | M | A | A | A | A | A | A | U | M | M | M | U |
|  | 6 m | O | O | O | O | O | O | O | O | O | O | O | O | O |
| RT BG | | | | | | | | | | | | | | |
| < 125 | 2 w | A | A | A | A | A | A | O | U | U | A | A | A | U |
| < 135 | 4 w | A | A | A | A | A | A | U | U | U | A | A | A | U |
| < 160 | 3 m | A | A | A | M | A | A | U | M | U | A | A | A | U |
|  | 6 m | O | O | O | O | O | O | O | O | O | O | O | O | O |
| Staining | 2 w | A | A | A | A | A | A | A | A | A | A | U | A | A |
|  | 4 w | A | A | M | A | A | A | A | A | M | A | U | A | M |

TABLE I-continued

| | | Control-Glass | AF Acrylic | H Styrene | D Styrene | Topas 1 | Topas 2 | PETG | A Polypro | F Polypro | LCP | Polycarbonate | Clear ABS | SBC |
|---|---|---|---|---|---|---|---|---|---|---|---|---|---|---|
| | 3 m | M | A | M | M | M | M | M | M | U | U | U | A | U |
| | 6 m | O | O | O | O | O | O | O | O | O | O | O | O | O |
| 50° C. CA | | | | | | | | | | | | | | |
| 38–52 | 2 w | A | A | A | A | A | A | A | U | U | A | A | A | U |
| 38–52 50° C. BG | 4 w | A | A | M | M | A | A | A | U | U | A | M | A | U |
| < 250 | 2 w | A | A | A | A | A | A | U | U | U | A | M | U | U |
| < 300 | 4 w | A | A | M | A | A | A | U | U | U | A | M | U | U |
| 50° C. Staining | 2 w | A | A | A | A | A | A | A | U | U | A | U | A | U |
| | 4 w | A | A | A | A | A | A | A | U | U | A | U | A | U |

Legend:
RT = Room Temperature
CA = Contact Angle
BG = Background Fluorescence
A = Acceptable
U = Unacceptable
M = Marginal
F = Further testing required
O = Not tested
2 w = 2 weeks
4 w = 4 weeks
3 m = 3 months
6 m = 6 months The AF Acrylic material tested was Plexiglass® V825 available from ATOFINA Chemicals, the H Styrene tested was product number 101–300 available from Huntsman Corporation, the D Styrene tested was DOW STYRON 695, the Topas 1 tested was TOPAS® grade 8007 S04 made by Ticona of Summit, N.J., the Topas 2 tested was TOPAS® grade 8007 D61 made by Ticona of Summit, N.J., the PETG tested was EASTAR® copolyester MN058 made by Eastman Chemical, the A polypro tested was Achieve 1615 polypropylene available from ExxonMobil®, the F polypro tested was Fina EOD 0017, an isotactic form of copolymer polypropylene made via a metallocene catalyst process available from Atofina, the LCP tested was Vectra® LCP liquid crystal copolymer available from Ticona, the polycarbonate tested was Bayer Makrolon 2508—available from Bayer, the clear ABS tested was Polylac PA1717C from Chi Mei Industries Co. Ltd., and the SBC compound tested was a K-resin substitute formulated by Compounding Solutions in Lewiston, Me.

Figure 2:
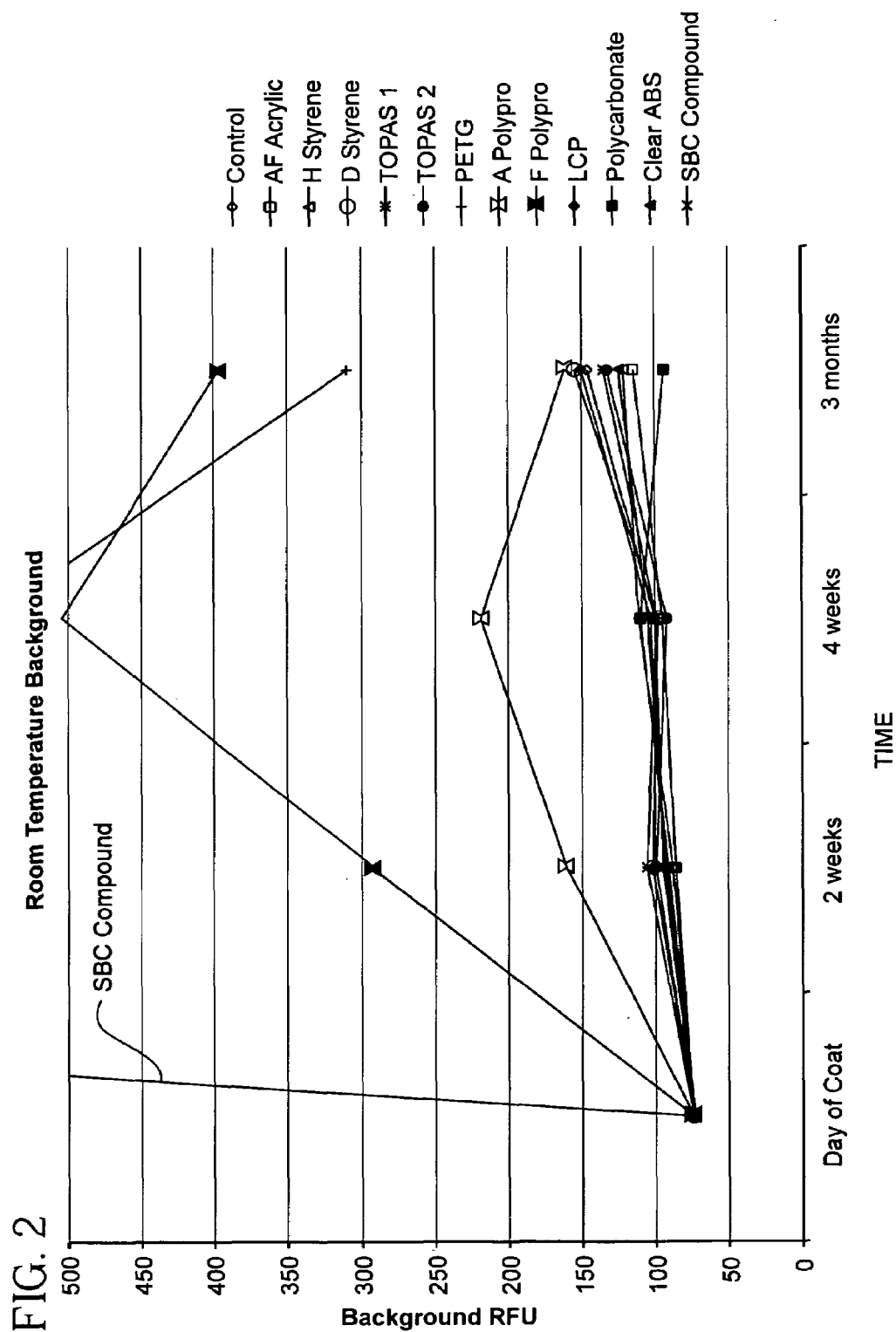
FIG. 2 is a graph of background fluorescence versus time for glass slides stored at room temperature with a variety of polymeric materials and a control material.

FIG. 2 is a graph showing the background fluorescence of glass slides stored with various materials for periods of 2 weeks, 4 weeks and 3 months. Initial background fluorescence readings were about 75 RFU for all samples. Acceptable materials produced a change in background fluorescence that was less than about 75 to 80 RFU for each of the time intervals measured compared to the control. The background fluorescence data is discussed further below with respect to FIG. 8.

Figure 3:
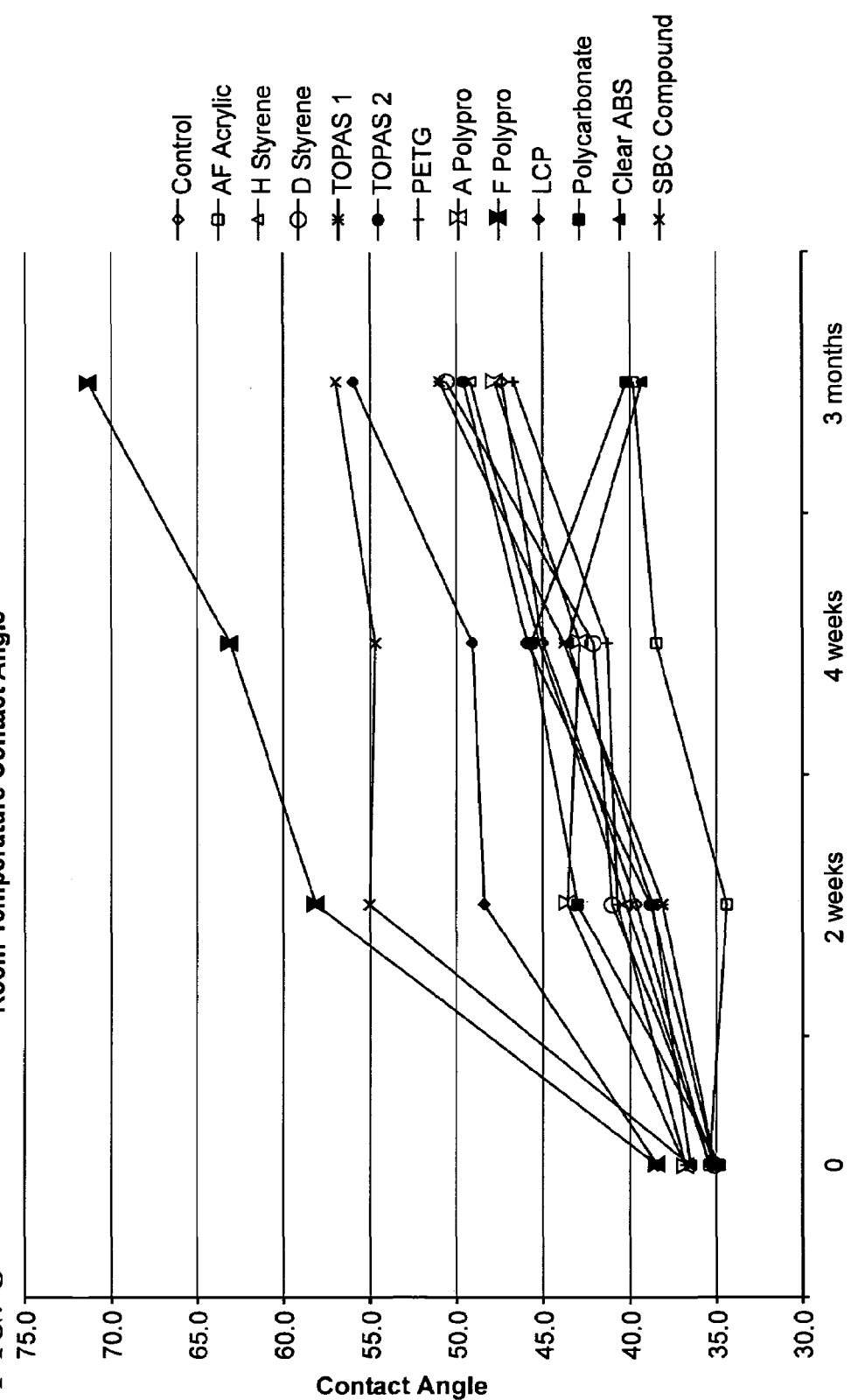
FIG. 3 is a graph of water contact angle versus time for glass slides stored at room temperature with a variety of polymeric materials and a control material.
Figure 7:
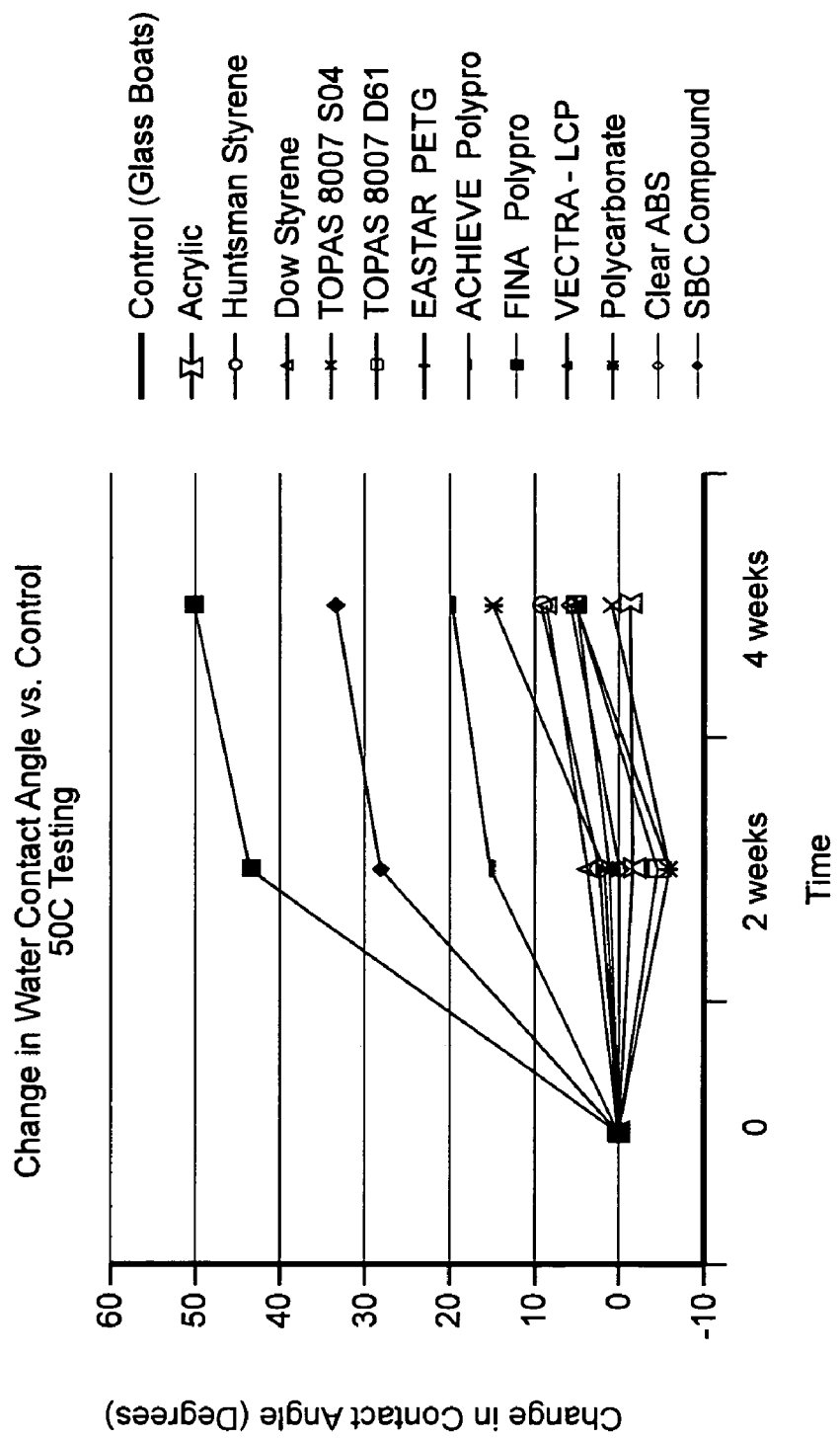
FIG. 7 is a graph of change in water contact angle versus time for glass slides stored at 50° C. with a variety of polymeric materials and a control material.

FIG. 3 is a graph of water contact angle versus time for slides stored at room temperature for 2 week, 4 weeks and 3 months. Each of the samples tested were either acceptable or marginally acceptable, except for the F polypro sample and the SBC compound. The AF acrylic material was the only material to produce results that were consistently lower than the control, indicating that this sample should be retested. FIG. 7 shows the change in water contact angle of slides stored at room temperature with each of the materials. Acceptable samples exhibited a change in contact angle of no more than 12 degrees greater than the change in water contact angle of slides stored in a sealed glass container (the control) at room temperature for up to 3 months. For certain preferred materials, the change in water contact angle on slides stored with the materials was no greater than 8 degrees greater than control slides stored in for up to 3 months at room temperature. For certain highly preferred materials stored with slides for up to 3 months at room temperature, the slides exhibited a change in contact angle of no more than 4 degrees greater than the change in contact angle of control slides stored at room temperature for 3 months.

Figure 4:
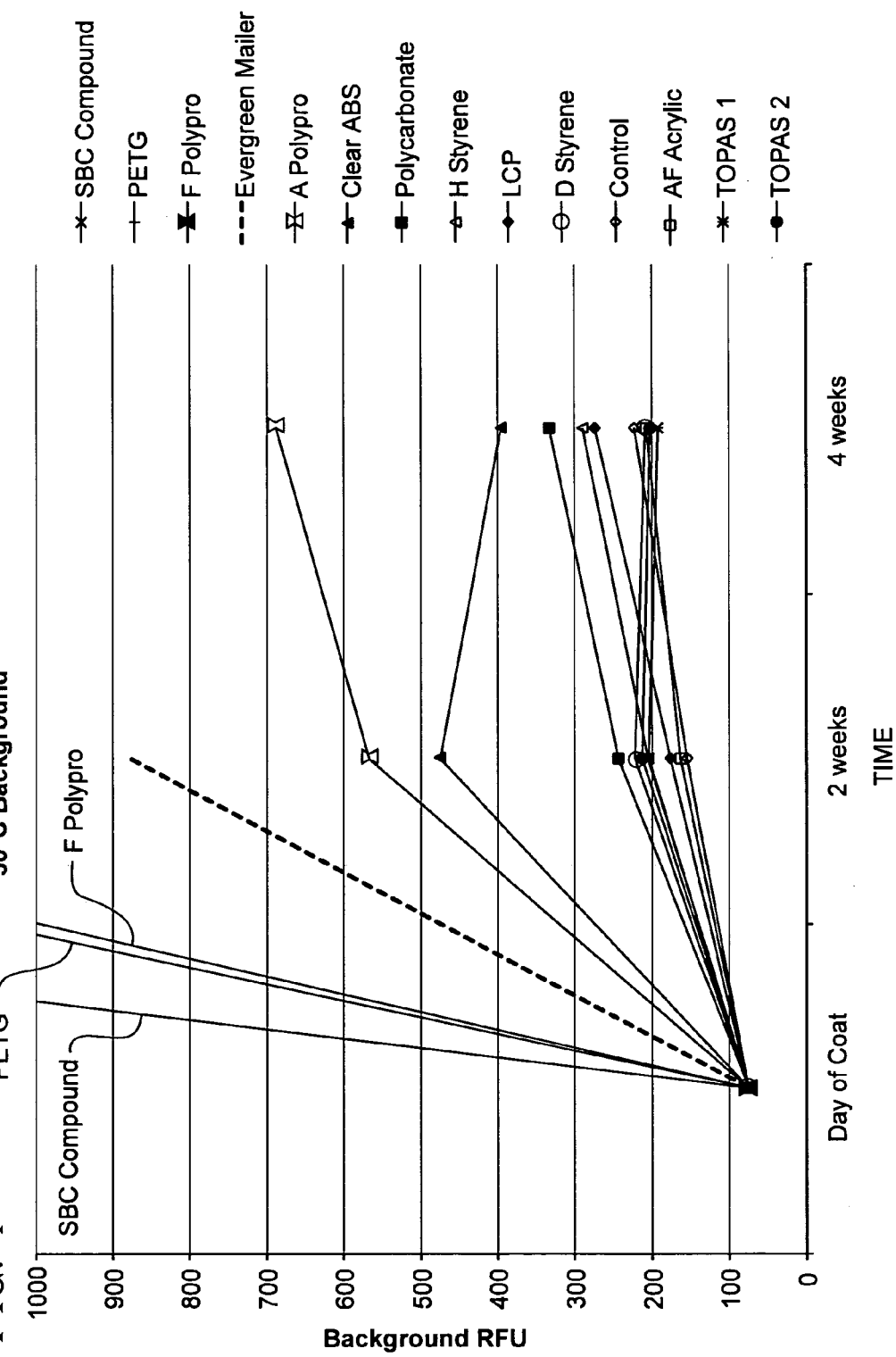
FIG. 4 is a graph of background fluorescence versus time for glass slides stored at 50° C. with a variety of polymeric materials and a control material.
Figure 5:
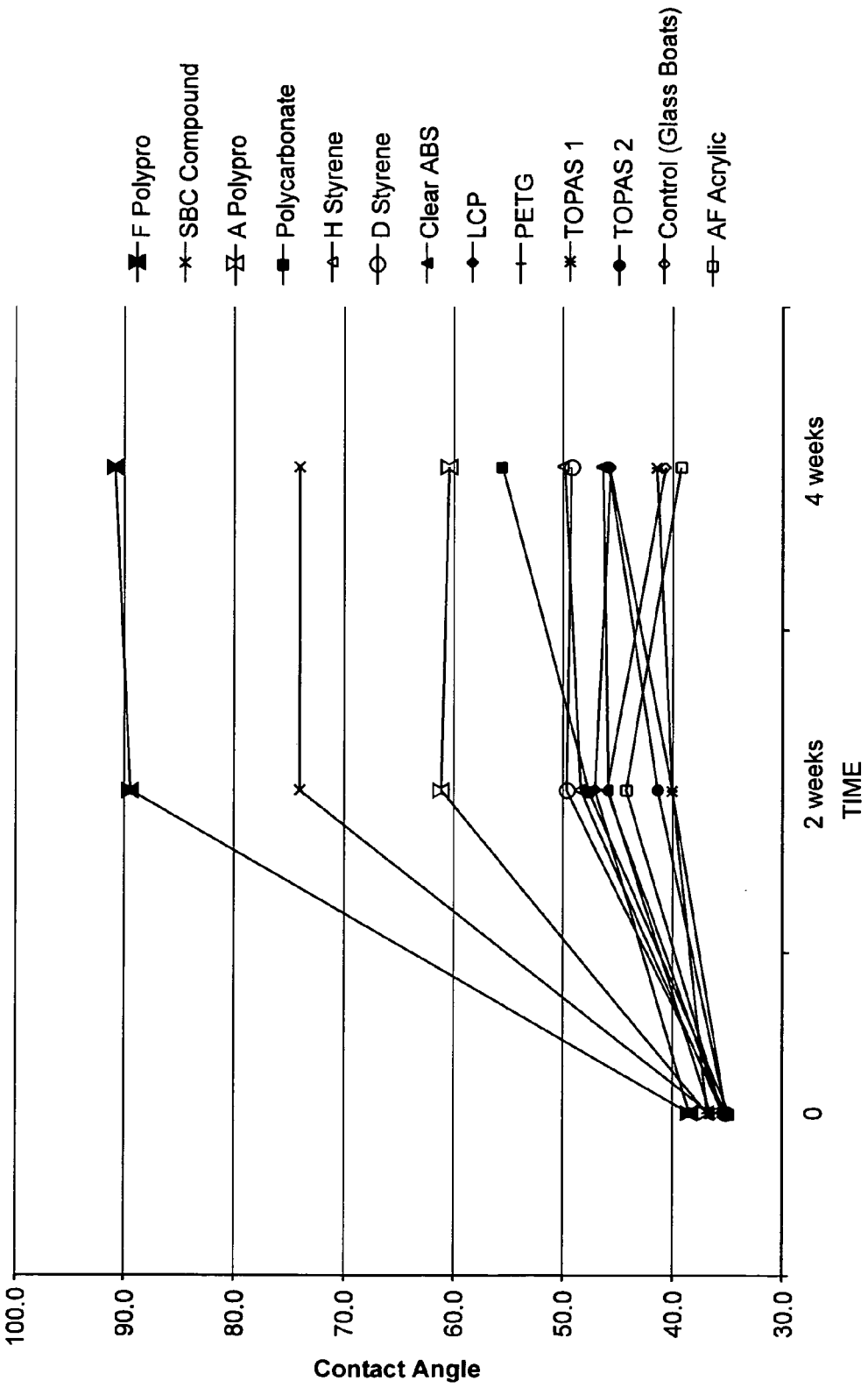
FIG. 5 is a graph of water contact angle versus time for glass slides stored at 50° C. with a variety of polymeric materials and a control material.
Figure 6:
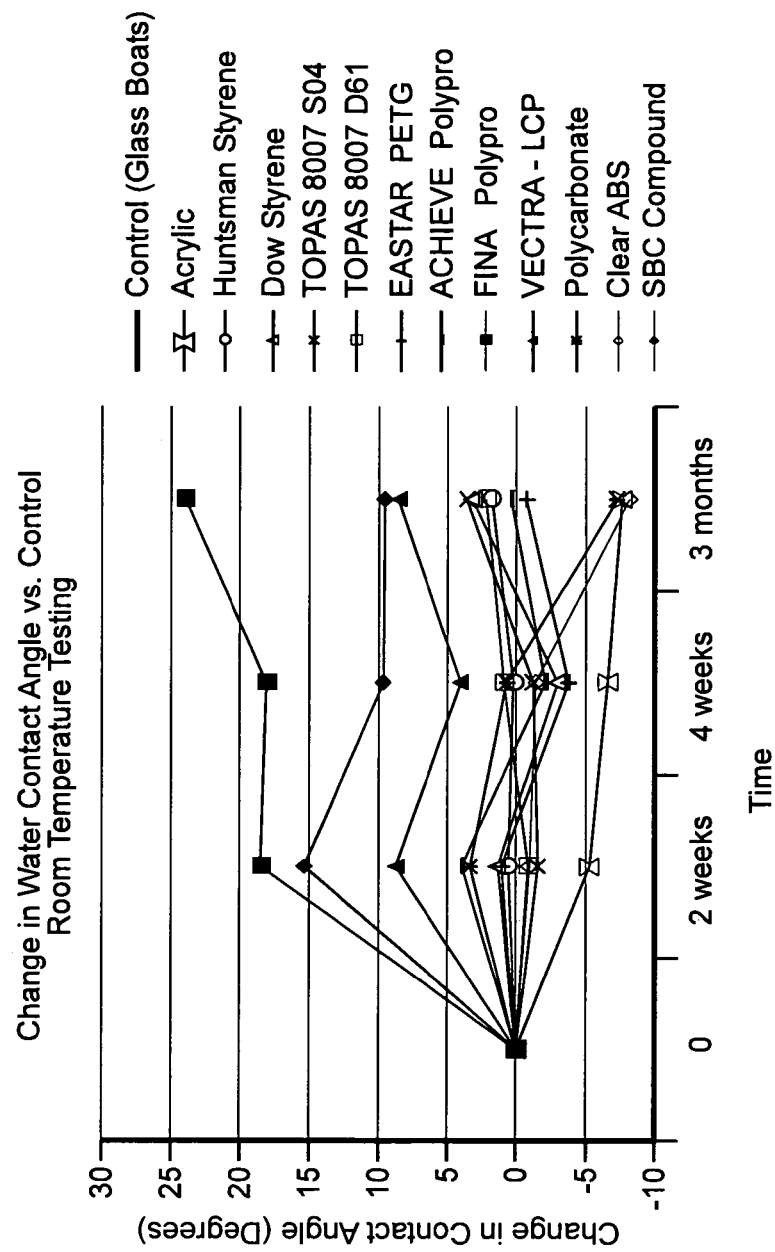
FIG. 6 is a graph of change in water contact angle versus time for glass slides stored at room temperature with a variety of polymeric materials and a control material.

FIG. 4 is graph of background fluorescence versus time for samples held at 50° C. for 2 weeks and 4 weeks. All samples were acceptable or marginally acceptable, except for the polyethylene Terephthalate, Glycol modified (PETG), A polypro, F polypro, clear ABS and SBC compound. FIG. 5 is a graph of water contact angle on the glass slides for samples held at 50° C. for 2 weeks and 4 weeks. All samples were acceptable or marginally acceptable except for A polypro, F Polypro, and the SBC compound. FIG. 7 shows the change in contact angle over time for slides stored with various material samples at 50° C. compared to a control, which were slides stored in a glass container. Acceptable materials caused the slides to exhibit a change in water contact angle of no more than about 10 degrees greater than the control after storage with the samples for up to 4 weeks. For certain preferred materials, the change in water contact angle of slides stored with these materials for up to 4 weeks at 50° C. was no more than about 5 degrees greater than the control.

Figure 8:
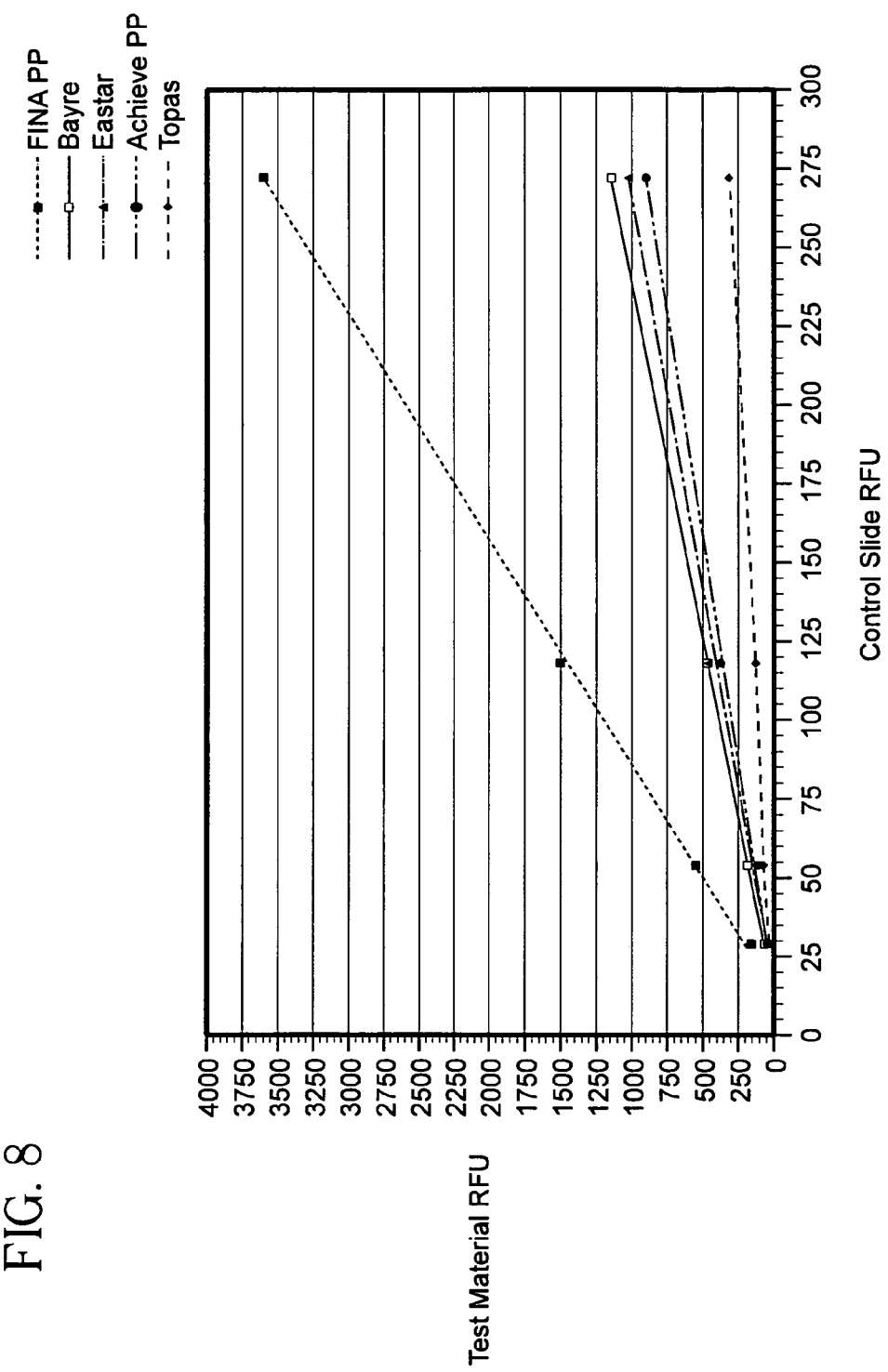
FIG. 8 is a graph of test material RFU versus control material RFU showing slides tested under the same conditions for various photomultiplier tube settings.

FIG. 8 is a graph of test material background fluorescence (RFU) versus control slide background fluorescence for samples stored six months. The control was slides stored in a glass container. The data was generated in different scanners at the same operating conditions. During the course of experimentation, the inventors evaluated the change in background fluorescence due to different packaging materials over time for both room temperature and 50° C. storage conditions. Using a specific lab scanner gives results that are adequate to separate the effects of the different materials on the coated slides. However, absolute RFU values at a given voltage setting will differ, sometimes greatly, from one scanner to another. Applicants observed that results may differ considerably even between two scanners of the same model operating under essentially the same conditions.

Applicants, therefore, developed a method that quantifies the effect of different packaging configurations on background fluorescence that is independent of the scanner used in the test. This method assumes that: (1) multiple photomultiplier tube (PMT) voltage settings are used in the comparison test (settings of 550, 650, 750, and 850 were used in this experiment); and that (2) the slides subjected to specific packaging conditions are compared to "control" slides that have been sealed in glass containers. While the absolute RFU values of all samples grow at an exponential rate as the voltage level increases, the relationship between RFU levels from the test packaging materials slides and the control slides is linear, as shown in FIG. 8. This relationship is defined by the simple equation $y=mx+b$, where y is the RFU value of the test material slide, x is the RFU value of the control slide, m is the slope of the linear relationship, and b is the value of y when $x=0$. As the control slide RFU (x) changes with voltage increases, the test slide RFU (y) increases at a rate defined by the slope (m). It is the slope (m) that effectively quantifies the packaging effect in a way that is independent of test scanner. If, for example, the slope for a given packaging material was estimated to be 3.45, it would simply mean that background RFU values for those slides could be expected to increase at a rate nearly 3.5 times that of the control slides. An increase of 10 RFU units for the control slides would mean an increase of about 34.5 RFU units for the test slides.

For the samples shown in FIG. 8, PMT settings of 550, 650, 750, and 850 were used for two different scanners. As is known by those skilled in the art, increasing the PMT setting of the scanner increases the background fluorescence of the slides measured. As shown in FIG. 8, a linear relationship exists between the increase in background fluorescence as measured by a scanner as a function of increasing photomultiplier tube (PMT) setting of slides stored for six months in a container made from the material and the increase in background fluorescence as measured by a scanner at increasing photomultiplier tube settings of slides stored for six months in a glass container. As discussed above, this relationship is defined by the equation, $y=mx+b$, where y is the background fluorescence value in RFUs of a slide stored with the material, x is the background fluorescence value of a slide stored in a glass container, m is the slope of the linear relationship, and b is the value of y when $x=0$. Applicants have determined that slides stored with acceptable materials had m values of less than or equal to about 3, 2.5 and 2.

It will be apparent to those skilled in the art that various modifications and variations can be made to the present invention without departing from the spirit or scope of the invention. For example, a variety of polymeric materials in addition to the specific examples provided herein may be used as materials for slide containers in accordance with the present invention provided they do not degrade the surface of slides stored therein. Thus, it is intended that the present invention cover modifications and variations of this invention provided they come within the scope of the appended claims and their equivalents.

What is claimed is:

1. A method of packaging slides which have a coating or monolayer on a surface thereof and adapted for the attachment of biomolecules to the surface comprising: enclosing a plurality of the slides in a container that does not degrade the ability of biomolecules to attach or bind to the surfaces of the slides when the slides are stored in the container for at least four weeks, wherein the slides are adapted for printing of microarrays of biomolecules and wherein the slides exhibit a change in water contact angle of no more than 12 degrees greater than the change in water angle of slides stored in a sealed glass container after storage in the containers at room temperature for up to 3 months.

2. A method of packaging slides which have a coating or monolayer on a surface thereof and adapted for the attachment of biomolecules to the surface comprising: enclosing a plurality of the slides in a container that does not degrade the ability of biomolecules to attach or bind to the surfaces of the slides when the slides are stored in the container for at least four weeks, wherein the slides are adapted for printing of microarrays of biomolecules and wherein the slides exhibit a change in water contact angle of no more than 8 degrees greater than the change in water angle of slides stored in a sealed glass container after storage in the containers at room temperature for up to 3 months.

* * * * *